United States Patent
Toriumi

(10) Patent No.: US 11,839,215 B2
(45) Date of Patent: Dec. 12, 2023

(54) URACIL COMPOUND AND HARMFUL ARTHROPOD CONTROL COMPOSITION CONTAINING SAME

(71) Applicant: Sumitomo Chemical Company, Limited, Tokyo (JP)

(72) Inventor: Tatsuya Toriumi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 574 days.

(21) Appl. No.: 16/973,968

(22) PCT Filed: Jun. 10, 2019

(86) PCT No.: PCT/JP2019/022937
§ 371 (c)(1),
(2) Date: Dec. 10, 2020

(87) PCT Pub. No.: WO2019/240081
PCT Pub. Date: Dec. 19, 2019

(65) Prior Publication Data
US 2021/0244027 A1   Aug. 12, 2021

(30) Foreign Application Priority Data
Jun. 11, 2018 (JP) ................................. 2018-110921

(51) Int. Cl.
A01N 43/50    (2006.01)
C07D 401/12   (2006.01)

(52) U.S. Cl.
CPC ........... *A01N 43/50* (2013.01); *C07D 401/12* (2013.01)

(58) Field of Classification Search
CPC .............................. A01N 43/50; C07D 401/12
See application file for complete search history.

(56) References Cited

U.S. PATENT DOCUMENTS 6,537,948 B1   3/2003  Tohyama et al.
2017/0327471 A1  11/2017  Alig et al.

FOREIGN PATENT DOCUMENTS

JP   2001270867 A   10/2001
JP   2002155061 A    5/2002
WO   2016037997 A1   3/2016

OTHER PUBLICATIONS

Office Action dated Feb. 23, 2022 in IN Application No. 202147000160.
Office Action with Search Report dated Jan. 4, 2023 in CN Application No. 201980038289.7.
English Translation of International Preliminary Report on Patentability dated Dec. 15, 2020 in International Application No. PCT/JP2019/022937.
English Translation of International Search Report dated Aug. 27, 2019 in International Application No. PCT/JP2019/022937.

*Primary Examiner* — James D. Anderson
(74) *Attorney, Agent, or Firm* — Panitch Schwarze Belisario & Nadel LLP

(57) ABSTRACT

A compound represented by the following formula (A) has excellent control efficacy against harmful arthropods.

(A)

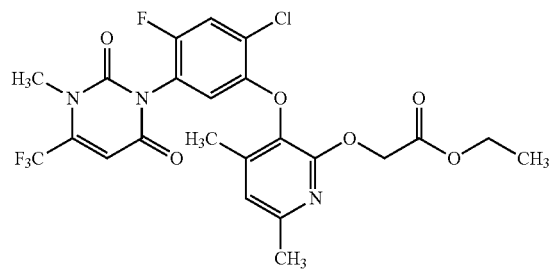

3 Claims, No Drawings

URACIL COMPOUND AND HARMFUL ARTHROPOD CONTROL COMPOSITION CONTAINING SAME

CROSS-REFERENCE TO RELATED APPLICATIONS

This application is a Section 371 of International Application No. PCT/JP2019/022937, filed Jun. 10, 2019, which was published in the Japanese language on Dec. 19, 2019 under International Publication No. WO 2019/240081 A1, which claims priority under 35 U.S.C. § 119(b) to Japanese Application No. 2018-110921, filed on Jun. 11, 2018, the disclosures of which are incorporated herein by reference in their entireties.

TECHNICAL FIELD

The present invention relates to a uracil compound and a composition for controlling harmful arthropods comprising the same.

BACKGROUND ART

To date, in order to control harmful arthropods, some compounds have been developed and come into practical use (see Non-patent document 1). Also, a compound represented by formula (B):

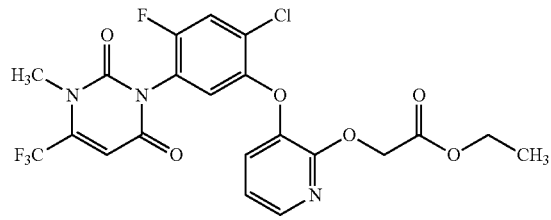

(B)

(hereinafter, referred to as Compound B) is described as a herbicide (see Patent document 1).

CITATION LIST

Patent Document

Patent Document 1: U.S. Pat. No. 6,537,948 B2

Non-Patent Document

Non-Patent Document 1: The Pesticide Manual—16th edition (published by BCPC) ISBN 978-1-901396-86-7

SUMMARY OF THE INVENTION

Problems to be Solved by Invention

An object of the present invention is to provide a compound having excellent control efficacy on harmful arthropods.

Means to Solve Problems

The present inventor has intensively studied the above-mentioned problems, and found that a compound represented by the following formula (A) has some excellent efficacy on controlling harmful arthropods, which thus completed the present invention.

The present invention is as follows.

[1] A compound represented by formula (A):

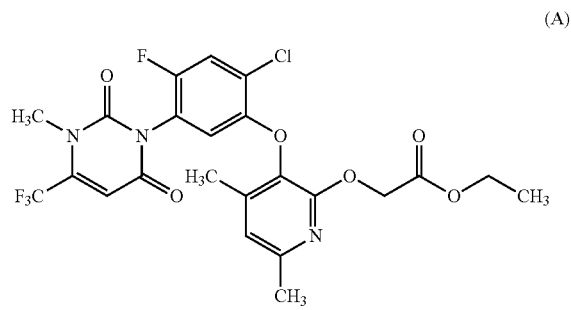 [SMILES: CCOC(=O)COc1nc(C)cc(C)c1Oc1cc(-n2c(=O)cc(C(F)(F)F)n(C)c2=O)c(F)cc1Cl]

(A)

(hereinafter, referred to as "Compound A").

[2] A composition comprising the compound represented by formula (A) according to [1] and an inert carrier (hereinafter, referred to as "Present composition A" or "Composition A of the present invention").

[3] A method for controlling harmful arthropod which comprises applying an effective amount of the compound according to [1] to a harmful arthropod or a habitat where a harmful arthropod lives (hereinafter, referred to as "Present control method" or "Control method of the present invention").

Effect of Invention

The present invention can control harmful arthropods.

MODE FOR CARRYING OUT THE INVENTION

The composition A of the present invention comprises the compound A and an inert carrier. The composition A of the present invention is usually prepared by mixing the compound A with an inert carrier such as solid carrier or liquid carrier, and if necessary, adding surfactants and the other auxiliary agents for formulation, to formulate into emulsifiable concentrates, oil solutions, dust formulations, granules, wettable powders, water dispersible granules, flowables, dry flowables, microcapsules and the others. These formulations comprises usually 0.1 to 99% by weight of the compound A of the present invention.

Examples of the solid carrier to be used in the formulation include fine powders or granules of clays (for example, kaolin clay, diatomaceous earth, bentonite, Fubasami clay, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol or ethanol); ketones (for example, acetone or methyl ethyl ketone); aromatic hydrocarbons (for example, toluene, xylene, ethyl benzene or methylnaphthalene); aliphatic hydrocarbons (for example, hexane, cyclohexane or kerosene); esters (for example, ethyl acetate or butyl acetate); nitriles (for example, acetonitrile or isobutyronitrile); ethers (for example, diisopropyl ether or diethyleneglycol dimethyl ether); amides (for example, N,N-dimethylformamide or N,N-dimethylacetamide); sulfoxides (for example, dimethyl sulfoxide); propylene carbonate; and vegetable oils (for example, soybean oil or cottonseed oil).

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer, and specific examples thereof include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the harmful arthropods on which the compound A has efficacies include the followings.

Hemiptera Pests:
- Delphacidae (for example, *Laodelphax striatellus*, *Nilaparvata lugens*, *Sogatella furcifera*, *Peregrinus maidis*, *Javesella pellucida*, *Perkinsiella saccharicida*, or *Tagosodes orizicolus*);
- Cicadellidae (for example, *Nephotettix cincticeps*, *Nephotettix virescens*, *Nephotettix nigropictus*, *Recilia dorsalis*, *Empoasca onukii*, *Empoasca fabae*, *Dalbulus maidis*, or *Cofana spectra*);
- Cercopidae (for example, *Mahanarva posticata*, or *Mahanarva fimbriolata*);
- Aphididae (for example, *Aphis fabae*, *Aphis glycines*, *Aphis gossypii*, *Aphis pomi*, *Aphis spiraecola*, *Myzus persicae*, *Brachycaudus helichrysi*, *Brevicoryne brassicae*, Rosy apple aphid (*Dysaphis plantaginea*), *Lipaphis erysimi*, *Macrosiphum euphorbiae*, *Aulacorthum solani*, *Nasonovia ribisnigri*, *Rhopalosiphum padi*, *Rhopalosiphum maidis*, *Toxoptera citricidus*, *Hyalopterus pruni*, *Melanaphis sacchari*, *Tetraneura nigriabdominalis*, *Ceratovacuna lanigera*, or *Eriosoma lanigerum*);
- Phylloxeridae (for example, *Daktulosphaira vitifoliae*, Pecan phylloxera (*Phylloxera devastatrix*), Pecan leaf phylloxera (*Phylloxera notabilis*), or Southern pecan leaf phylloxera (*Phylloxera russellae*));
- Adelgidae (for example, *Adelges tsugae*, *Adelges piceae*, or *Aphrastasia pectinatae*);
- Pentatomidae (for example, *Scotinophara lurida*, Malayan rice black bug (*Scotinophara coarctata*), *Nezara antennata*, *Eysarcoris aeneus*, *Eysarcoris lewisi*, *Eysarcoris ventralis*, *Eysarcoris annamita*, *Halyomorpha halys*, *Nezara viridula*, Brown stink bug (*Euschistus heros*), Red banded stink bug (*Piezodorus guildinii*), *Oebalus pugnax*, *Dichelops melacanthus*);
- Cydnidae (for example, Burrower brown bug (*Scaptocoris castanea*));
- Alydidae (for example, *Riptortus pedestris*, *Leptocorisa chinensis*, or *Leptocorisa acuta*);
- Coreidae (for example, *Cletus punctiger*, or *Leptoglossus australis*);
- Lygaeidae (for example, *Caverelius saccharivorus*, *Togo hemipterus*, or *Blissus leucopterus*);
- Miridae (for example, *Trigonotylus caelestialium*, *Stenotus rubrovittatus*, *Stenodema calcarata*, or *Lygus lineolaris*);
- Aleyrodidae (for example, *Trialeurodes vaporariorum*, *Bemisia tabaci*, *Dialeurodes citri*, *Aleurocanthus spiniferus*, *Aleurocanthus camelliae*, or *Pealius euryae*);
- Diaspididae (for example, *Abgrallaspis cyanophylli*, *Aonidiella aurantii*, *Diaspidiotus perniciosus*, *Pseudaulacaspis pentagona*, *Unaspis yanonensis*, or *Unaspis citri*);
- Coccidae (for example, *Ceroplastes rubens*);
- Margarodidae (for example, *Icerya purchasi*, or *Icerya seychellarum*);
- Pseudococcidae (for example, *Phenacoccus solani*, *Phenacoccus solenopsis*, *Planococcus kraunhiae*, *Planococcus comstocki*, *Planococcus citri*, *Pseudococcus calceolariae*, *Pseudococcus longispinus*, or *Brevennia rehi*);
- Psyllidae (for example, *Diaphorina citri*, *Trioza erytreae*, *Cacopsylla pyrisuga*, *Cacopsylla chinensis*, *Bactericera cockerelli*, or *Pear psylla* (*Cacopsylla pyricola*));
- Tingidae (for example, *Corythucha ciliata*, *Corythucha marmorata*, *Stephanitis nashi*, or *Stephanitis pyrioides*);
- Cimicidae (for example, *Cimex lectularius*);
- Cicadidae (for example, Giant Cicada (*Quesada gigas*)); and
- *Triatoma* spp. (for example, *Triatoma infestans*).

Lepidoptera
- Crambidae (for example, *Chilo suppressalis*, Darkheaded stem borer (*Chilo polychrysus*), White stem borer (*Scirpophaga innotata*), *Scirpophaga incertulas*, *Rupela albina*, *Cnaphalocrocis medinalis*, *Marasmia patnalis*, *Marasmia exigua*, *Notarcha derogata*, *Ostrinia furnacalis*, European corn borer (*Ostrinia nubilalis*), *Hellula undalis*, *Herpetogramma luctuosale*, *Pediasia teterrellus*, *Nymphula depunctalis*, or Sugarcane borer (*Diatraea saccharalis*));
- Pyralidae (for example, *Elasmopalpus lignosellus*, *Plodia interpunctella*, or *Euzophera batangensis*);
- Noctuidae (for example, *Spodoptera litura*, *Spodoptera exigua*, *Mythimna separata*, *Mamestra brassicae*, *Sesamia inferens*, *Spodoptera mauritia*, *Narange aenescens*, *Spodoptera frugiperda*, *Spodoptera exempta*, *Agrotis Autographa nigrisigna*, *Plusia festucae*, Soybean looper (*Chrysodeixis includens*), *Trichoplusia* spp., *Heliothis* spp. (for example, *Heliothis virescens*), *Helicoverpa* spp. (for example, *Helicoverpa armigera*, or *Helicoverpa zea*), Velvetbean caterpillar (*Anticarsia gemmatalis*), Cotton leafworm (*Alabama argillacea*), or Hop vine borer (*Hydraecia immanis*)),
- Pieridae (for example, *Pieris rapae*);
- Tortricidae (for example, *Grapholita molesta*, *Grapholita dimorpha*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, Bean Shoot Borer (*Epinotia aporema*), or Citrus fruit borer (*Ecdytolopha aurantiana*));
- Gracillariidae (for example, *Caloptilia theivora*, or *Phyllonorycter ringoniella*);
- Carposinidae (for example, *Carposina sasakii*);
- Lyonetiidae (for example, Coffee Leaf miner (*Leucoptera coffeela*), *Lyonetia clerkella*, or *Lyonetia prunifoliella*);
- Lymantriidae (for example, *Lymantria* spp. (for example, *Lymantria dispar*), or *Euproctis* spp. (for example, *Euproctis pseudoconspersa*));

Pluteliidae (for example, *Plutella xylostella*);
Gelechiidae (for example, *Anarsia lineatella, Helcystogramma triannulellum, Pectinophora gossypiella, Phthorimaea operculella,* or *Tuta absolut*);
Arctiidae (for example, *Hyphantria cunea*);
Castniidae (for example, Giant Sugarcane borer (*Telchin licus*));
Cossidae (for example, *Cosus insularis*);
Geometridae (for example, *Ascotis selenaria*);
Limacodidae (for example, *Parasa lepida*);
Stathmopodidae (for example, *Stathmopoda masinissa*);
Sphingidae (for example, *Acherontia lachesis*);
Sesiidae (for example, *Nokona feralis, Synanthedon hector,* or *Synanthedon tenuis*);
Hesperiidae (for example, *Parnara guttata*); and
Tinedae (for example, *Tinea translucens* or *Tineola biselliella*).
Thysanoptera
Thripidae (for example, *Frankliniella occidentalis, Thrips palmi, Scirtothrips dorsalis, Thrips tabaci, Frankliniella intonsa, Stenchaetothrips biformis,* or *Echinothrips americanus*); and
Phlaeothripidae (for example, *Haplothrips aculeates*).

The method for controlling harmful arthropods of the present invention comprises an applying of an effective amount of the compound A to harmful arthropods directly, and/or to a habitat where a harmful arthropod lives (such as plants or soil).

An application dose of the compound A is usually within a range of 1 to 10,000 g per 10,000 m². When the compound A is formulated into emulsifiable concentrates, wettable powders, flowables, and the others, such formulations are usually applied after it with water in such a way that a concentration of the active ingredient is within a range from 0.01 to 10,000 ppm, and in the vase of being formulated into dust formulations, granules, and the others, such formulations are used at itself.

Also, the composition of the present invention may be used as an agent for controlling harmful arthropods in agricultural lands such as fields, paddy fields, turfs, and orchards.

EXAMPLES

Hereinafter, the present invention is explained in more detail by using Preparation Example, Formulation Example, and Test Example and the like, however, the present invention should not be limited to these examples.

The Preparation Examples of the compound A are shown.

To a solution of 30% hydrogen bromide in acetic acid 11.47 g were added dropwise a mixture of 2-{2-chloro-4-fluoro-5-[3-methyl-2,6-dioxo-4-(trifluoromethyl)-1,2,5,6-tetrahydropyrimidin-1-yl]phenoxy}-3-oxobutanamide 2.00 g, which was prepared according to a method described in U.S. Pat. No. 7,189,855, acetyl acetone 0.64 g, and acetic acid 4.02 g at room temperature. The resulting mixture was warmed to 50° C., and stirred for 5 hours. The resulting mixture was concentrated under reduced pressure, and to the residue were added methanol and water, and the mixture was neutralized with 4N aqueous sodium hydroxide solution. The resulting solids were filtered, and the filtered substances were washed with water, and dried under reduced pressure to obtain an intermediate compound A represented by the following formula 1.31 g.

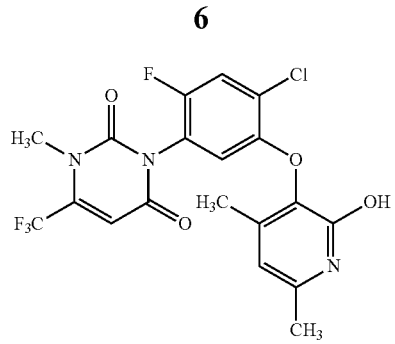

Intermediate Compound A

To a mixture of the intermediate compound A 1.03 g, xylene 4.03 g, and boron trifluoride diethyl ether complex 0.03 g are added dropwise a solution of 40% ethyl diazoacetate in xylene 0.90 g at 50° C., and the mixture was stirred for 3 hours. To the resulting mixtures were added 10% aqueous sulfuric acid solution, and the mixture was separated with a separatory funnel. To the resulting organic layers are added ethyl acetate, and the mixture was washed with sodium bicarbonate water and water successively, and concentrated under reduced pressure. The resulting residue was subjected to a silica gel column chromatography to obtain the compound A 0.87 g.

$^1$H-NMR data of the compound A is indicated below.
$^1$H-NMR (CDCl$_3$) δ:7.34 (1H, d, J=8.8 Hz), 6.77 (1H, d, J=6.2 Hz), 6.65 (1H, s), 6.26 (1H, s), 4.90-4.76 (2H, m), 4.12 (2H, q, J=7.0 Hz), 3.48 (3H, s), 2.33 (3H, s), 2.18 (3H, s), 1.23 (3H, t, J=7.0 Hz).

Next, Formulation Examples of the compound A are described. Herein, the term "part(s)" means "part(s) by weight".

Formulation Example 1

Into a mixture of 35 parts of xylene and 35 parts of N,N-dimethylformamide, ten parts of the compound A is added, followed by mixing, and then 14 parts of polyoxyethylene styryl phenyl ether and 6 parts of calcium dodecylbenzene sulfonate are added, followed by mixing them to obtain a formulation.

Formulation Example 2

Four (4) parts of sodium lauryl sulfate, 2 parts of calcium lignin sulfonate, 20 parts of wet silica and 54 parts of diatomaceous earth are mixed, and further 20 parts of the compound A is added, followed by mixing them to obtain a formulation.

Formulation Example 3

To 2 parts of the compound A, 1 part of wet silica, 2 parts of calcium lignin sulfonate, 30 parts of bentonite and 65 parts of kaolin clay are added, followed by mixing. Then an appropriate amount of water is added to the mixture, and the resulting mixture is further stirred, and is granulated with a granulator, and is forced-air dried to obtain a formulation.

Formulation Example 4

Into an appropriate amount of acetone, 1 part of the compound A is added, followed by mixing, and then 5 parts of wet silica, 0.3 parts of isopropyl acid phosphate and 93.7 parts of kaolin clay are added, followed by mixing with stirring thoroughly and removal of acetone from the mixture by evaporation to obtain a formulation.

Formulation Example 5

Thirty-five (35) parts of a mixture of polyoxyethylene alkyl ether sulfate ammonium salt and wet silica (weight ratio of 1:1), 20 parts of the compound A, and 45 parts of water are mixed thoroughly to obtain a formulation.

Further, Test Examples are used to show an efficacy of the compound A on controlling harmful arthropods.

Test Example 1

The compound A is made to a formulation according to a similar method to that described in the Formulation Example 5, and thereto is added water containing 0.03 v/v % of shindain (registered trademark) to prepare a diluted solution containing 500 ppm of the test compound.

The diluted solution was sprayed into the cabbage (*Brassicae oleracea*) seedling (on the developmental stage of the second to third true leaf) that is planted in a container in a ratio of 20 mL/seedling.

Thereafter, the stem and leaf thereof was cut out and then was installed into the container that was covered with the filter paper. Five common cutworms (*Spodoptera litura*) at the second instar larval stages were released into the container, and the container was allowed to stand at 25° C. for 5 days. Thereafter, the surviving insects were counted, and the mortality of insects was calculated by the following equation, and as a result, the mortality was shown to be 100%.

Mortality (%)={1−Number of the surviving insects/5}×100

Comparative Test Example 1

The test was conducted by using the compound B in place of the compound A according to a similar method to that described in Test Example 1, and as a result, the mortality was shown to be 0%.

INDUSTRIAL APPLICABILITY

The compound A shows an excellent control effect against a harmful arthropod.

The invention claimed is:

1. A compound represented by formula (A):

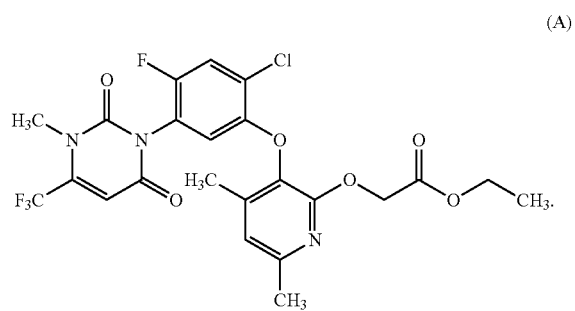 [SMILES: CCOC(=O)COc1nc(C)cc(C)c1Oc1cc(-n2c(=O)cc(C(F)(F)F)n(C)c2=O)c(F)cc1Cl]

(A)

2. A composition comprising the compound represented by formula (A) according to claim 1 and an inert carrier.

3. A method for controlling harmful arthropod which comprises applying an effective amount of the compound according to claim 1 to a harmful arthropod or a habitat where a harmful arthropod lives.

* * * * *